US006929941B2

United States Patent
Odom

(12) United States Patent
(10) Patent No.: US 6,929,941 B2
(45) Date of Patent: Aug. 16, 2005

(54) CHIMERIC CELL-TARGETING PATHOGENIC ORGANISM AND METHOD OF THERAPEUTIC USE

(75) Inventor: Duncan Odom, Cambridge, MA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/672,408

(22) Filed: Sep. 26, 2003

(65) Prior Publication Data

US 2004/0067217 A1 Apr. 8, 2004

Related U.S. Application Data

(62) Division of application No. 10/002,389, filed on Nov. 30, 2001, now Pat. No. 6,638,756.
(60) Provisional application No. 60/297,995, filed on Jun. 13, 2001, and provisional application No. 60/251,523, filed on Dec. 5, 2000.

(51) Int. Cl.[7] ............................. C12N 1/14; C12N 1/16; C12N 1/18; C12N 1/20
(52) U.S. Cl. ............................ 435/252.3; 435/254.1; 435/254.22
(58) Field of Search .................... 435/252.3, 254.1, 435/254.22

(56) References Cited

U.S. PATENT DOCUMENTS

| 6,083,751 A | 7/2000 | Feldhaus et al. |
| 6,346,411 B1 | 2/2002 | Hostetter et al. |

OTHER PUBLICATIONS

Lo et al (Mol. Biol. Cell vol. 9, pp 161–171, 1998).*
Gale et al., "Linkage of Adhesion, Filamentous Growth, and Virulence in *Candida albicans* to Single Gene, *INT1*," *Science*, 279:1355–1358 (1998).
Moritz et al., "Cytotoxic T lymphocytes with a grafted recognition specificity for ERBB2–expressing tumor cells," *Proc. Natl. Acad. Sci. USA*, 91:4318–4322 (1994).

Wels et al., "Biotechnological and gene therapeutic strategies in cancer treatment," *Gene* 159:73–80 (1995).
Calderone et al., "Adherence and Receptor Relationships of *Candida albicans*", *Microbiol. Rev.*, 55(1):1–20 (1991).
Gale et al., "Linkage of Adhesion, Filamentous Growth, and Virulence in *Candida albicans* to a Single Gene, *INT1*," *Science*, 279:1355–1358 (1998).
Moritz et al., "Cytotoxic T lymphocytes with a grafted recognition specificity for ERBB2–expressing tumor cells," *Proc. Natl. Acad. Sci. USA*, 91:4318–4322 (1994).
Wels et al., "Biotechnological and gene therapeutic strategies in cancer treatment," *Gene* 159:73–80 (1995).
Sonneborn et al., "Control of White–Opaque Phenotypic Switching in *Candida albicans* by the Efg1p Morphogenetic Regulator", *Infect. Immun.*, 67(9):4655–4660 (1999).

* cited by examiner

*Primary Examiner*—Mark Navarro
(74) *Attorney, Agent, or Firm*—DLA Piper Rudnick Gray Cary US LLP

(57) ABSTRACT

The invention chimeric organism comprises a chimeric surface integrin-like fusion protein in which the I domain has been replaced by an antibody fragment that binds a disease-associated antigen on a cell. Binding of the antibody fragment to the disease-associated antigen triggers virulent transformation of the chimeric pathogenic organism so as to cause the organism to infiltrate the target cell with specificity. Preferably, the chimeric organism is a chimeric pathogenic *C. albicans* having an INT1 fusion protein in which the I domain is replaced by an antibody fragment, preferably a single chain antibody, and in which expression of an iron transporter gene necessary for infiltration of a target cell is triggered under the control of a EFG1p response element. Binding of the antibody to the disease-associated antigen causes filamentous transformation in the chimeric pathogenic *C. albicans* and specific infiltration of target cells. The invention chimeric pathogenic organisms are used in therapeutic methods to specifically infiltrate and destroy diseased cells to which the antibody fragment binds while remaining non-pathogenic to normal cells.

5 Claims, 26 Drawing Sheets

Figure 3:
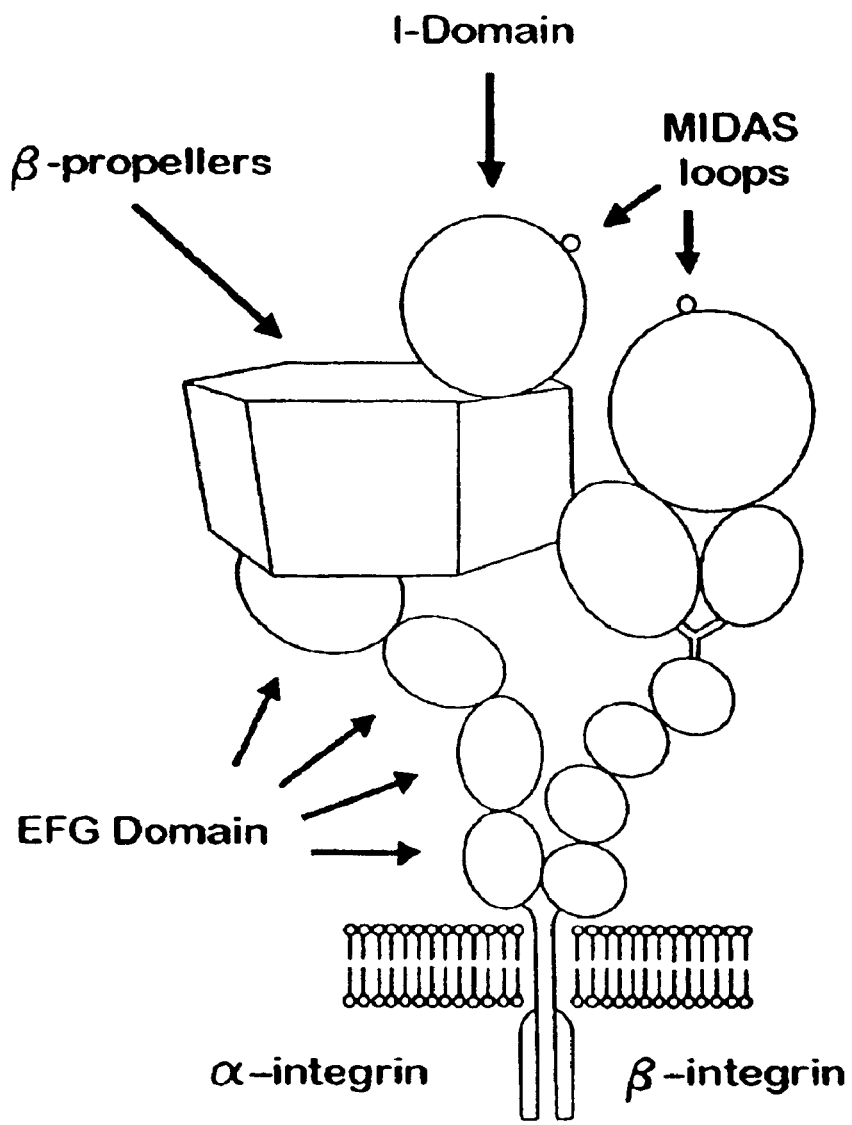

```
                                        Rsa I
                                        Sca I                        Mse I  Mse I  Hinf
I                                                                                    I
                                         ||                           |     |       |
cccaaaaaagataaaataaaaacaaaacaaaacaaaagtactaacaaattattgaaacttttaattttttaataaagaatc
80 gggtttttctattttattttgtttgtttgttttcatgattgtttaataactttgaaaattaaaaattatttcttag
      •         •         •         || •         •           •|    |  •     |
                                     37                       61    68       76
                                     38
     Sau3A I
     Mbo I
     Dpn I
     BstY I
     Bgl II      Mse I
      ||         | agtagatctattgttaaaagaaatgaactcaactccaagtaaattattaccgatagataaacattctcatttacaattac
160
tcatctagataacaattttctttacttgagttgaggttcatttaataatggctatctatttgtaagagtaaatgttaatg
     ||   •     |     •         •         •         •         •         •
     84         94
     84
     85
     85
     85
                     SfaN I
            Sec I          Mse I
     Mnl I  Mnl I   Ssp I                                            Xmn I
      |     |   |    |                                                | agcctcaatcgtcctcggcatcaatatttaattccccaacaaaaccattgaatttccccagaacaaattccaagccgagt
240
tcggagttagcaggagccgtagttataaattaaggggttgttttggtaacttaaaggggtcttgtttaaggttcggctca
     |     •   |    |•    |  •    |  •        •         •          •|        •
     163       173        183                                       221
               173        188
                   178
     Sau3A I
```

FIG. 1-1

```
Mbo I
Dpn I
Alw I                                              Sau3A I
BstY I        Alu I         Mae I                  Mbo I                    Mbo II
 ||            |              |                    Dpn I                      |
                                                     | ttagatccaaattcaagctctgatacctacactagcgaacaagatcaagagaaagggaaagaagagaaaaaggacacagc
320 aatctaggtttaagttcgagactatggatgtgatcgcttgttctagttctctttcccttcttctcttttcctgtgtcg
 ||      •     | •       •|    •|     •        •|       •
 •
    243        256         272    283              301
    244               283
    244               283
    244
    244
                              Sau3A I
                              Mbo I              Taq I
         Tth111 II            Dpn I              Cla I       Tth111 II
           |                    |                 ||            | ctttcaaacatcttttgatagaaattttgatcttgataattcaatcgatatacaacaaacaattcaacatcagcaacaac
400 gaaagtttgtagaaaactatctttaaaactagaactattaagttagctatatgttgtttgttaagttgtagtcgttgttg
  |     •     •      |•      •    ||     •     |     •
  •
        325           349         364           376
                      349         365
                      349
                                  Mse I                      Tth111 II
Taq I
 |                                 |                            |              | agccacaacaacaacaacaactctcacaaaccgacaataatttaattgatgaattttcttttcaaacaccgatgacttcg
480 tcggtgttgttgttgttgttgagagtgtttggctgttattaaattaactacttaaaagaaaagtttgtggctactgaagc
  •       •        •       •|       •     |     •     |
  •
                                  442         463
478
        Tth111 II                          Nla III               Mnl I
          |                                   |                    |
```

FIG. 1-2

```
actttagacctaaccaagcaaaatccaactgtggacaaagtgaatgaaaatcatgcaccaacttatataaatacctcccc
560 tgaaatctggattggttcgttttaggttgacacctgtttcacttacttttagtacgtggttgaatatatttatggagggg
      •   |   •       •     •       •  |    •        •       •    |
 •
             495                                      532                   554
                                 Hph I
                                 Mae III
                                 Hga I                                Mae III
                                 | ||                                    | caacaaatcaataatgaaaaaggcaactcctaaagcgtcacctaaaaaagttgcatttactgtaactaatcccgaaattc
640 gttgtttagttattacttttccgttgaggatttcgcagtggattttttcaacgtaaatgacattgattagggctttaag
      •       •       •       |  ||  •      •        •      •  |        •
 •
                              595                                622
                                597
                                598
                              Sau3A I
                      Mnl I    Mbo I
                      Taq I    Dpn I
                 Ple I         Mbo II              Hinf I
                 Hinf I  Mbo II         HinC II    Mbo II                  Mse I
                 |   |   |   |   |       |          |   |                    | atcattatccagataatagagtcgaggaagaagatcaaagtcaacaaaaagaagattcagttgagccacccttaatacaa
720 tagtaataggtctattatctcagctccttcttctagtttcagttgttttcttctaagtcaactcggtgggaattatgtt
      •       |•  |   |   |   |   |        •|   |     •          • |
 •
             659    667       680            691                        712
             659       670                       694
                662       673
                   664       673
                                673
          Sau3A I
          Mbo I
          Dpn I
          Alw I
          BstY I                              Mbo II
          | |                                  |
```

FIG. 1-3

```
catcaatggaaagatccttctcaattcaattattctgatgaagatacaaatgcttcagttccaccaacaccaccacttca
800 gtagttacctttctaggaagagttaagttaataagactacttctatgtttacgaagtcaaggtggttgtggtggtgaagt
       • ||       •         •       |       •          •       •
        732                          760
         733
         733
         733
         733
              HinP I
              Hha I                                   Mnl I
              Fsp I                           Nla IV
              ||                               |    | tacgacgaaacctacttttgcgcaattattgaacaaaaacaacgaagtcaatctggaaccagaggcattgacagatatga
880 atgctgctttggatgaaaacgcgttaataacttgtttttgttgcttcagttagaccttggtctccgtaactgtctatact
            •   ||   •      •    •    •   |  •   |    •
             819                           855
              820                                      862
              820
         BstU I
         HinP I
         Hha I
      Mse I                                  Dde I
       |    ||                                  | aattaaagcgcgaaaatttcagcaatttatcattagatgaaaaagtcaatttatatcttagtcccactaataataacaat
960 ttaatttcgcgcttttaaagtcgttaaatagtaatctacttttcagttaaatatagaatcagggtgattattattgtta
    |    ||•      •       •       •       •    •       |  •        •
     883                                                937
          888
          888
          889
                  Sau3A I
                  Mbo I
                  Dpn I                     Taq I
                  BstY I                    BstB I                 Ssp I
                  Alw I              Hga I                         Xmn I
```

FIG. 1-4

```
                        ||              |  ||              |  |
agtaagaatgtgtcagatatggatctgcatttacaaaacttgcaagacgcttcgaaaaacaaaactaatgaaaatattca
1040
tcattcttacacagtctatacctagacgtaaatgttttgaacgttctgcgaagcttttgttttgattacttttataagt
    •         •||    •         •       | •||       •         | |
              981                    1006                  1030
              981                    1011                  1033
              982                    1012
              982
              982
           Mse I
           Dra I                     Mse I
Mse I
          ||                            |
|
caatttgtcatttgctttaaaagcaccaaagaatgatattgaaaacccattaaactcattgactaacgcagatattctgt
1120
gttaaacagtaaacgaaattttcgtggtttcttactataacttttgggtaatttgagtaactgattgcgtctataagaca
                ||  •         •         •      |          •        •
|
                1056                             1090
1120
                1057

Hph I
                                                                              Mae
III
                                                                           Sec I
              Sau3A I                                                      ScrF I
 Sau3A I      Mbo I                                                        EcoR II
 Mbo I        Dpn I                                              AlwN I    BstE
II
 Dpn I        Alw I                       Mnl I                  Hinf I    BstN I
 |            ||                          |                      |  |    |  |||
taagatcatctggatcatcacaatcgtcattacaatctttgaggaatgacaatcgtgtcttggaatcagtgcctgggtca
1200
attctagtagacctagtagtgttagcagtaatgttagaaactccttactgttagcacagaaccttagtcacggacccagt
 |   • ||   •        •        •|         •          • |  |  •|    |||
•
 1124 1132                    1161                    1183        1192
```

FIG. 1-5

```
                1124        1133                                              1187      1196
                1124        1133                                                   1192
                            1133                                                   1192
                                                                                   1192
1197

1198
                        ScrF I
                        EcoR II
                        BstN I
    Dde I       Mse I                                            Mnl I       Hinf I
Mnl I
    |           |   |                                            |           |           |
cctaagaaggttaatcctggattgtctttgaatgacggcataaaggggttctctgatgaggttgttgaatcattacttcc
1280 ggattcttccaattaggacctaacagaaacttactgccgtatttccccaagagactactccaacaacttagtaatgaagg
 |•          •|      |    •          •          •          •        |•          | •
|•
    1202        1211                                             1258       1267
1279
                        1216
                        1216
                        1216
                        Taq I
                        Xho I
                        PaeR7 I                      SfaN I
    Mae III     Ava I                                Nla III
SfaN I
    |           ||                                   |    |                          | tcgtgacttatctcgagacaaattagagactacaaaagaacatgatgcaccagaacacaacaatgagaattttattgatg
1360 agcactgaatagagctctgtttaatctctgatgttttcttgtactacgtggtcttgtgttgttactcttaaaataactac
    |       •||     •      •           •|  |    •          •       •           |
•
    1283        1292                                1321
1357
                1292                                1324
                1292
                1293
                                                                        Sau3A I
                                                            Sau3A I
                                                            Mbo I      Mbo I
                                                                        Dpn I
```

FIG. 1-6

```
                                        Dpn I    Ple I    Alw I
     Taq I              Dde I           Bcl I    Hinf I   BstY I
     |                  |               | |      |        | | ctaaatcgactaataccaataagggacaactcttagtatcatctgatgatcatttggactctttttgatagatcctataac
1440 gatttagctgattatggttattccctgttgagaatcatagtagactactagtaaacctgagaaaactatctaggatattg
     |    •      •    •  |    •      | |  •     |   •       | |
•
     1366              1392          1407      1417        1429
                                     1408      1417        1430
                                     1408                  1430
                                     1408                  1430
                                                           1430
                                                 Nsi I
           Hinf I          SfaN I                Mse I
           |               |                     | | cacactgaacaatcaattttgaatctttttgaatagtgcatcacaatctcaaatttcgttaaatgcattggaaaaacaaag
1520 gtgtgacttgttagttaaaacttagaaaacttatcacgtagtgttagagtttaaagcaatttacgtaaccttttttgtttc
      •     •  •|       •    |   •          • |   •  |   •
•
            1461            1477                1498
                                                 1502
                    Fnu4H I       Mbo II
    Tth111 II       Tth111 II AlwN I Mbo II                         Mse I
    |               |         | |    | |                            | gcaaacacaggaacaagaacaaacacaagcggcagagcctgaagaagaaacttcgtttagtgataatatcaaagttaaac
1600 cgtttgtgtccttgttcttgtttgtgttcgccgtctcggacttcttctttgaagcaaatcactattatagtttcaatttg
    |    •    |      |•  |    •| |  •          •          •        |
•
    1522     1540      1553 1561                                    1595
                 1549       1564
                                                 Sec I
                                                 Hae III
                                                 Hae I
                           Mae III               Eae I
                           BstE II       Xmn I   Bal I              Alu I
                           | |           |       | | |              |
```

FIG. 1-7

```
aagagccaaagagcaatttggagtttgtcaaggttaccatcaagaaagaaccagttctggccacggaaataaaagctcca
1680 ttctcggtttctcgttaaacctcaaacagttccaatggtagttctttcttggtcaagaccggtgcctttattttcgaggt
       •         •         •  ||     •      | •      ||•|       •    |
                           1632        1648      1658              1674
                             1633                1658
                                                 1658
                                                 1659
                                                 1661
                                                 Alu I
                 Ssp I                           Pvu II
             Taq I  Mse I         Mbo II         NspB II      Fok I
             |  |   |             |              ||           | aaaagagaatttttcaagtcgaatattaagaataaaaaatgaagatgaaattgccgaaccagctgatattcatcctaaaaa
1760 ttttctcttaaaagttcagcttataattcttattttttacttctactttaacggcttggtcgactataagtaggattttt
        •    | •|   |       •         |         •        ||         |
        1698  1705          1720              1739            1750
           1701                               1739
                                              1740
              Mbo II
         Nla III             Nsi I                     Hinf I
      Tth111 II  Taq I      SfaN I     Mbo II    Mse I    Mnl I
      |         |   ||      ||         |         |        |  | agaaaatgaagcaaacagtcatgtcgaagatactgatgcattgttgaagaaagcacttaatgatgatgaggaatctgaca
1840 tcttttacttcgtttgtcagtacagcttctatgactacgtaacaacttctttcgtgaattactactactccttagactgt
    •         •|    |   ||    •  ||   •      |    •      |   •       | •|
    1772          1784    1795       1806     1817        1828
             1780         1796                            1831
                  1786
                                                    Mbo II
                                                    Bbv II
                                                    | cgacccaaaactcaacgaaaatgtcaattcgttttcatattgatagtgattggaaattggaagacagtaatgatggcgat
1920
```

FIG. 1-8

```
gctgggttttgagttgcttttacagttaagcaaaagtataactatcactaacctttaaccttctgtcattactaccgcta
                                                                  |
                                                                  1900
                                                                  1900

Mae III
    Mbo II                                              Mae II
Hph I
    |                                                      |
| | agagaagataatgatgatatttctcgttttgagaaatcagatatttgaacgacgtatcacagacttctgatattattgg
                                                                             2000 tctcttctattactactataaagagcaaaactctttagtctataaaacttgctgcatagtgtctgaagactataataacc
| |                                                |
  1924                                             1973
1999
2000
                                                        Sau3A I
                                                        Mbo I
                                                        Dpn I
EcoR I
    |                                                      |                | tgacaaatatggaaactcatcaagtgaaataaccaccaaaacattagcaccccaagatcggacaacaatgacaaggaga
                                                                        2080 actgtttataccttgagtagttcactttattggtggttttgtaatcgtgggggttctagcctgttgttactgttcctct
|•                                                          |  •
                                                            2057
2079
                                                            2057
                                                            2057
                    Sau3A I                                 Rsa I
                    Mbo I                                   Nla IV
                    Dpn I                                   Kpn I
                    Alw I                                   Ban I
                    BstY I                                  Asp718
                    Mbo II   Alu I       Hinf I   Mnl I              Mbo II
                     | ||      |           |       | ||                 |
```

FIG. 1-9

```
attctaaatctttggaagatccagctaataatgaatcattgcaacaacaattggaggtaccgcatacaaaagaagatgat
2160 taagatttagaaaccttctaggtcgattattacttagtaacgttgttgttaacctccatggcgtatgttttcttctacta
              · | || · |     · |     ·      · | || ·           · |
              ·
              2095    2103    2113                2134              2152
                 2097                              2136
                 2098                              2136
                 2098                              2136
                 2098                              2136
                 2098                              2137
                    Ssp I         Mbo II
                      |             | agcattttagccaactcgtccaatattgctccacctgaagaattgactttgcccgtagtggaagcaaatgattattcatc
2240 tcgtaaaatcggttgagcaggttataacgaggtggacttcttaactgaaacgggcatcaccttcgtttactaataagtag
       ·    · |       ·       | ·      ·      ·       ·        ·
·
            2182           2197
                                                      HgiA I
                                              Mbo II  Bsp1286 I
          Mae II        Nsi I      Alu I  Ple I   Mae I
     Mse I   Mae III    SfaN I    HinD III Hinf I  Xba I         Hinf I
       |     | |         | |      | |     | |     | |   |          | ttttaatgacgtgaccaaaacttttgatgcatactcaagctttgaagagtcattatctagagagcacgaaactgattcaa
2320 aaaattactgcactggttttgaaaactacgtatgagttcgaaacttctcagtaatagatctctcgtgctttgactaagtt
·       |    |·|      · ||  ·    || ·    | |    · ||  · |      · |
·
     2243    2251    2266     2277    2287    2296              2314
           2249       2267     2278    2287    2297
                                       2284           2302
                                                      2302

Sau3A I
      Mse I
Mbo I
       Ase I                              Mbo II
Dpn I
       | |                                  |
  |
```

FIG. 1-10 aaccaattaatttcatatcaatttggcataaacaagaaaagcagaagaaacatcaaattcataaagttccaactaaacag
2400 ttggttaattaaagtatagttaaaccgtatttgttcttttcgtcttctttgtagtttaagtatttcaaggttgatttgtc
| |    •    •    •    •   |   •    •    •    •
|      2326                                2364
2400
       2327
2400

2400
                                                            Mae I
                                                            Spe I
                      Mae I                     Hinf I     Mae III
                        |                          |         |  || atcattgctagttatcaacaatacaaaaacgaacaagaatctcgtgttactagtgataaagtgaaaatcccaaatgccat
2480 tagtaacgatcaatagttgttatgttttgcttgttcttagagcacaatgatcactatttcacttttagggtttacggta
      |    •    •    •    •    |   •    |  ||    •    •
 •
      2408                          2437   2446
                                           2449
                                           2450
                                    Mbo II                    Fok I
                Mnl I      Nla III                           Nla III
                  |          |       |                         | | acaattcaagaaattcaaagaggtaaatgtcatgtcaagaagagttgttagtccagacatggatgatttgaatgtatctc
2560 tgttaagttctttaagtttctccatttacagtacagttcttctcaacaatcaggtctgtacctactaaacttacatagag
 •         •    |    •|     |•    •       | •|     •
           2500      2511                         2538
                           2519                      2541
                     Ple I
                     Hinf I
                     Mbo II      Mse I
                     Bbv II      Dra I
                      | |         || aattttaccagaattatctgaagactctggatttaaagatttgaattttgccaactactccaataacaccaacagacca
2640

FIG. 1-11

```
ttaaaaatggtcttaatagacttctgagacctaaatttctaaacttaaaacggttgatgaggttattgtggttgtctggt
              •|  |      •||       •         •         •         •
              2581       2593
              2581       2594
                 2584
                 2584
                                                          Sau3A I
                                                          Mbo I
              HgiA I           Ssp I                      Dpn I
              Bsp1286 I        Taq I                      Alw I              Mnl I
              |                |  |                       |                  | agaagttttactccattgagcactaaaaatgtcttgtcgaatattgataacgatcctaatgttgttgaacctcctgaacc
2720 tcttcaaaatgaggtaactcgtgattttacagaacagcttataactattgctaggattacaacaacttggaggacttgg
        •   | •        •      | |       • |      •        |
            2658               2677      2692             2710
            2658               2680      2692
                                         2692
                                         2692
                                         HinP I
                                         Hha I
                                         Hae II
                                         Fnu4H I         Nla IV
    Nde I          Mae I      Alu I      Bbv I           Ban I
    |              |          |          | ||            | gaaatcatatgctgaaattagaaatgctagacggttatcagctaataaggcagcgccaaatcaggcaccaccattgccac·
2800 ctttagtatacgactttaatctttacgatctgccaatagtcgattattccgtcgcggtttagtccgtggtggtaacggtg
      | •        •      | •        |         | ||        • |           •
      2726            2747       2760      2770         2784
                                            2770         2784
                                            2772
                                            2773
                                            2773

Xmn I
          Mbo II                                              Bsp1286 I
Mbo II
          |                                                   |              |
```

FIG. 1-12

```
cacaacgacaaccatcttcaactcgttccaattcaaataaacgagtgtccagatttagagtgcccacatttgaaattaga
2880 gtgttgctgttggtagaagttgagcaaggttaagtttatttgctcacaggtctaaatctcacgggtgtaaactttaatct
|·                                                                                    
            2815                                    2860
2879

2879
                              Nla III
                              NspH I
                              Nsp7524 I
              Mbo II          Mae III
  Xmn I                       Dra III   Afl III
    |    |                      |         | | agaacttcttcagcattagcaccttgtgacatgtataatgatattttgatgatttcggtgcgggttctaaaccaactat
2960 tcttgaagaagtcgtaatcgtggaacactgtacatattactataaaaactactaaagccacgcccaagatttggttgata
  |    |  ·        |         |  ||      ·         ·          ·          ·
  2882                2900     2909
         2887                  2906
                               2909
                               2909
                               2910

Ple I

Hinf I
                                              Mnl I    Bsm I        Mae
III                                                                 III
                                                |        |          | | aaaggcagaaggaatgaaaacattgccaagtatggataaagatgatgtcaagaggattttgaatgcaaagaaaggtgtga
3040 tttccgtcttccttactttgtaacggttcatacctatttctactacagttctcctaaaacttacgtttctttccacact
|·                                                            3012       3021
3037

3039
```

FIG. 1-13

3039

```
                                                                          Sau3A I
                                                                          Mbo I
                                       Sau3A I                            Dpn I
                                       Mbo I                              Alw I
                                       Dpn I                   Hph I      Mbo II
                                       Bcl I        EcoR I     Mae III    Bbv II
                                       ||           |          ||    |    |
ctcaagatgaatatataaatgccaaacttgttgatcaaaaacctaaaaagaattcaattgtcaccgatcccgaagaccga
3120 gagttctacttatatatttacggtttgaacaactagttttggatttttcttaagttaacagtggctagggcttctggct
   •                •      • ||         •    |         ||    |  • |
•
                                       3072         3090       3100       3112
                                       3073                    3101       3112
                                       3073                               3106
                                       3073                               3106
                                                                          3106
                                                                          3106
                                                                    Hae III
                                                                    Gdi II        Ple I
          Mbo II          Mnl I            Hinf I                   Eae I         Hinf I
          |               |                |                        ||            |
tatgaagaattacaacaaactgcctctatacacaatgccaccattgattcaagtatttatggccgaccagactccatttc
3200 atacttcttaatgttgtttgacggagatatgtgttacggtggtaactaagttcataaataccggctggtctgaggtaaag
   •        |     •  •    |    •      •   |    •            ||         |
•
        3124             3143              3166             3180          3190
                                                            3180          3190
                                                            3181

Nla III                                                     Sau3A I
          NspH I                                                      Mbo I
          Nsp7524 I                                                   Dpn I
          Afl III         Dde I                                       |
          ||              |
taccgacatgttgccttatcttagtgatgaattgaaaaaaccacctacggctttattatctgctgatcgtttgtttatgg
3280 atggctgtacaacggaatagaatcactacttaactttttggtggatgccgaaataatagacgactagcaaacaaatacc
```

FIG. 1-14

```
        ||  •           |        •         •         •         •   |   •
      3206          3220                                         3265
      3206                                                       3265
      3206                                                       3265
         3207
                                                    Sec I
                                                    ScrF I
                              Sau3A I                EcoR II
                              Mbo I                  BstN I
                Fok I         Dpn I                  Sec I       Fnu4H I
                Rsa I   Mse I                        Hph I       Bbv I       Mbo II   Mae
  III
                  |  |     |   |                     |  ||         |            |        |
``` aacaagaagtacatccgttaagatcaaactctgttttggttcacccaggggcaggagcagcaactaattcttcaatgtta
3360 ttgttcttcatgtaggcaattctagtttgagacaaaaccaagtgggtccccgtcctcgtcgttgattaagaagttacaat
```
   •               |•  |        |  •  |         •      •|  ||      •       |    •      |•       |
   •
              3289       3298                        3321            3337         3349
3357
                   3292       3302                   3324         3337
                              3302                   3325
                              3302                   3325
                                                     3325
                                                     3325
                    Mse I        BspM I
                    Ase I        Hph I    Mae I
                    | |          |  |     |
``` ccagagccagatttgaattaatcaattcacctgctagaaatgtgctgaacaacagtgataatgtcgccatcagtggtaa
3440 ggtctcggtctaaaacttaattagttaagtggacgatctttacacgacttgttgtcactattacagcggtagtcaccatt
```
   •             •    ||•      | |   |   •        •         •       •
                    3378     3388  3395
                    3379          3390
         Rsa I
         Sca I
     Mae I         Mse I                            Alu I
   BspM I
     | ||            |                                |
```

FIG. 1-15

```
tgctagtactattagttttaaccaattggatatgaattttgatgaccaagctacaattggtcaaaaaatccaagagcaac
3520 acgatcatgataatcaaaattggttaacctatacttaaaactactggttcgatgttaaccagttttttaggttctcgttg
  |  ||    •      | •       •        •      |•        •          •
|•
  3443        3458                                    3489
3519
      3445
        3446
                                                      HgiA I
                                                      Bsp1286 I
                                                      ApaL I
                                              Hae III
                                              Hae I
                                              Eae I
                              Hph I           Bal I
                                |              ||      | ctgcttcaaaatccgccaatactgttcgtggtgatgatgatggattggccagtgcacctgaaacaccaagaactcctacc
3600 gacgaagttttaggcggttatgacaagcaccactactacctaaccggtcacgtggactttgtggttcttgaggatgg
      •         •     |    •       ||  •  |        •          •
                      3550         3566    •
                                   3566
                                   3566
                                       3567
                                           3572
                                           3572
                                           3572
                                    Mbo II
      Ple I                Alu I              Mae I
      Hinf I   Tth111 II   HinD III   Mnl I           Hph I   Mse I    Hph
I
       |         |          ||    |    |      |        |       |        | aaaaaggagtccatatcaagcaagcctgccaagcttctctctgcctcccctagaaaatcaccaattaagattggttcacc
3680 ttttcctcaggtatagttcgttcggacggttcgaaagaagacggaggggatcttttagtggttaattctaaccaagtgg
     |  •      |  •    •|| |  •   |      |      |•     |    •    |
   3607       3617     3631    3644       3658  3665   3676
   3607                3632            3650
```

FIG. 1-16

```
                                    3637
                                  Sau3A I
                                   Mbo I
                                   Dpn I                                                Xmn I
       Taq I    Mse I              Alw I                                                Mbo II
         |       |                  ||                                                   | |
agttcgagttattaagaaaaatggatcaattgctggcattgaaccaatcccaaaagccactcacaaaccgaagaaatcat
3760 tcaagctcaataattctttttacctagttaacgaccgtaacttggttagggttttcggtgagtgtttggcttctttagta
    |   • |       •  ||     •         •         •        •              | |
    •
   3684     3692      3703                                             3750
                      3704                                                 3753
                      3704
                      3704
                                                                Sau3A I
                                                                 Mbo I
                                                                 Alw I
                                                                 Msp I
                                                                 Hpa II
       Sty I                                            Alu I    Dpn I
       Sec I                         Rsa I      Hph I   BspM II          SfaN I
         |                             |          |      |   ||  ||        |
tccaaggaaacgagatttcaaaccataaagtacgagatggtggaatttccaagctccggatcagagcatcaacagcat
3840 aggttcctttgctctaaagtttggtatttcatgctctaccaccttaaagtggttcgaggcctagtctcgtagttgtcgta
 .|      •         •           |       •       |•   |  || ||     |•
 •
  3762              3790                 3808      3817          3828
  3762                                            3814    3821
                                                  3818
                                                  3818
                                                          3820
                                                           3821
                                                            3821
                                 Xca I
              Mae I              Acc I   SfaN I         Nla IV
                |                  |       |              |
aatcctagtatggtttctgttccttcacagtatactgatgctacttcaacggttccagatgaaaacaaagatgttcaaca
3920 ttaggatcataccaaagacaaggaagtgtcatatgactacgatgaagttgccaaggtctacttttgtttctacaagttgt
```

FIG. 1-17

```
          .   |    .     .        |      |  .      .|    .         .
              3845              3870   3877      3891
                                3870

ScrF I
                                                                           Nci
   I
                                                                           Msp
   I
                                       Hph I                               Hpa
  II
      Mnl I                   SfaN I                                       Bcn
   I
       |                        |  |                                        | caagcctcgtgaaaagcaaaagcaaaagcatcaccatcgccatcatcatcatcatcataaacaaaaaactgatattccgg
4000 gttcggagcacttttcgttttcgttttcgtagtggtagcggtagtagtagtagtagtatttgttttttgactataaggcc
  .    |   .    .     |  •|   .     .      .        .       .        .    |
       3925                    3948
3997
                                3951
3997

3997

3997

3997
                       EcoN I                  Mnl I                     Mse I
                         |                       |                         |
gtgttgttgatgatgaaattcctgatgtaggattacaagaacgaggcaaattattctttagagttttaggaattaagaat
4080 cacaacaactactactttaaggactacatcctaatgttcttgctccgtttaataagaaatctcaaaatccttaattctta
  .        .    •|      .     .  |     .       .       .       .        . |
             4021              4043                                     4073
            Mse I            Hinf I    Mae II
            Ase I            Mbo II    Mse I                            Mae III
            I I                | |      | |                                |
```

FIG. 1-18

```
atcaatttacccgatattaatactcacaaaggaagattcactttaacgttggataatggagtgcattgtgttactacacc
                                                                              4160 tagttaaatgggctataattatgagtgtttccttctaagtgaaattgcaacctattacctcacgtaacacaatgatgtgg
       •    ||  •         •|  |  •  | |   •       •            |
•
           4096           4112     4123                         4150
             4097           4115     4126
                                              AlwN I
              Nla III                       HinC II       Hinf I
Mse I
  |                                            |  |        |
| agaatacaacatggacgaccataatgttgccataggtaaagaatttgagttgacagttgctgattcattagagtttattt
                                                                              4240 tcttatgttgtacctgctggtattacaacggtatccatttcttaaactcaactgtcaacgactaagtaatctcaaataaa
    |         •         •          •         |• |      •|       •
|
     4170                                   4209         4222
4240
                                          4214
                  Nde I
            SfaN I        Mnl I  Rsa I     Mae III
              |  |          |      |         | taactttgaaggcatcatatgaaaaacctcgtggtacattagtagaagtgactgaaaagaaagttgtcaaatcaagaaat
                                                                              4320 attgaaacttccgtagtatacttttggagcaccatgtaatcatcttcactgacttttctttcaacagtttagttcttta
     •|  |    •     |  •   |    •   |•      •       •
         4252            4267  4274         4288
           4256
                    Taq I
                    Sau3A I                                          Sec I
           Taq I    Mbo I                                            ScrF I
           Ple I    Dpn I                                            EcoR
II
           Hinf I   Alw I      Hph I         Bsp1286 I               BstN I
             | |    || |         |               |                     | agattgagtcgattatttggatcgaaagatattatcaccacgacaaagtttgtgcccactgaagtcaaagatacctgggc
                                                                              4400
```

FIG. 1-19

```
tctaactcagctaataaacctagcttctataatagtggtgctgtttcaaacacgggtgacttcagtttctatggacccg
 |  |•      || |        •    |     •         •|        •           •  |
 •
   4326         4339         4355         4372               4394
   4326         4340                                         4394
       4329    4340                                         4394
               4340                                         4394
                  4342

Msp I
                                                              Hpa II
                                    Mae III         Mbo II    Cfr10 I
                           Mae I                    Bbv II    Hph I
SfaN I
                             |       |                |        |  ||
 | taataagtttgctcctgatggttcatttgctagatgttacattgatttacaacaatttgaagaccaaatcaccggtaaag
4480 attattcaaacgaggactaccaagtaaacgatctacaatgtaactaaatgttgttaaacttctggtttagtggccatttc
         •          •          |     |    •       •        |•      |•||
 |
                            4430                                   4459      4469
4480
                                   4436                    4459      4471
                                                                       4472
                                                                       4472
           Sau3A I
           Mbo I
           Dpn I        Mse I                                       Mnl I
             |            |                                           | catcacagtttgatctcaattgttttaatgaatgggaaactatgagtaatggcaatcaaccaatgaaaagaggcaaacct
4560 gtagtgtcaaactagagttaacaaaattacttacccttgatactcattaccgttagttggttacttttctccgtttgga
    •   |     •   |    •       •         •        •         •         |
   4492       4505                                                    4550
   4492
   4492
                                                       Sau3A I
                                                       Mbo I
                                                       Dpn I
                                                       Alw I
Sau3A I
```

FIG. 1-20

```
                                              BstY I
Mbo I                                         Sau3A I
Dpn I                                         Mbo I
Alw I                    Mse I                Dpn I          Ssp I
BstY I
                           |                   |  ||           |
 ||
tataagattgctcaattggaagttaaaatgttgtatgttccacgatcagatccaagagaaatattaccaaccagcattag
4640 atattctaacgagttaaccttcaattttacaacatacaaggtgctagtctaggttctctttataatggttggtcgtaatc
    •    •    |    •    •    |   ||•         |         •
 ||                     4583           4604         4620
4639
                                       4604
4640
                                       4604
4640
                                                4608
4640
                                                4609
4640
                                                4609
                                                4609
                                                4609
                                                                            Hph
  I                                                                          Mnl I
       Nde I   SfaN I    Mse I                                              |  |
       |       |         |
atccgcatatgaaagcatcaatgaattaaacaatgaacagaataattactttgaaggttatttacatcaagaaggaggtg
4720 taggcgtatactttcgtagttacttaatttgttacttgtcttattaatgaaacttccaataaatgtagttcttcctccac
   |   •   |   •    |   •     •      •     •     •    ||
 •
       4646   4655   4666                                                  4715
4717
                               Bsp1286 I
                       Mse I
```

FIG. 1-21

```
                Mse I   Mae II      Ase I
Mae I
                  |       |          ||    |                                                            |
attgtccaatttttaagaaacgttttttcaaattaatgggcacttctttattggctcatagtgaaatatctcataaaact
4800 taacaggttaaaaattctttgcaaaaaagtttaattacccgtgaagaaataaccgagtatcactttatagagtattttga
 .      |       |       . ||    | .           .           .           .           .
|.
        4733    4740            4752
4799
                                 4753
                                     4758
                                                                    Sau3A I
             Mse I                                                  Mbo I
             Ase I                                                  Dpn I          Taq I
             ||                                                      |              |
agagccaaaattaatttatcaaaagttgttgatttgatttatgttgataaagaaaacattgatcgttccaatcatcgaaa
4880 tctcggttttaattaaatagttttcaacaactaaactaaatacaactatttctttttgtaactagcaaggttagtagctttt
              ||     .         .         .         .          .         .|      .  |
 .
             4810                                                          4861         4875
             4811                                                          4861
                                                                            4861
                       Nsi I
                       Nla III
                       Sau3A I
                       Mbo I
                       Dpn I                                                        HgiA I
                       Alw I  Bsm I                               Hph I             Bsp1286
I                       ||    ||   |                               |                  |
tttcagtgatgtgttattgttggatcatgcattcaaaatcaaatttgctaatggtgagttgattgatttttgtgctccta
4960 aaagtcactacacaataacaacctagtacgtaagttttagtttaaacgattaccactcaactaactaaaaacacgaggat
     .     .       . ||   || |.         .          .      |     .        .   .|
             4902   4909                        4933                    4952
             4903                                                       4952
             4903
             4903
```

FIG. 1-22

```
                                                                    Sty I
                                                                 HinC II
                                                                 Mae II  Nla III
                                                                 Aha II  Sec I
      Nla III              Hinf I                                Aat II  Nco I
        |                    |                                    || |   ||
   4906
   4907
ataaacatgaaatgaaaatatggattcaaaatttacaagaaattatctatagaaatcggttcagacgtcaaccatgggta
5040 tatttgtactttacttttatacctaagttttaaatgttctttaatagatatctttagccaagtctgcagttggtacccat
     |      •    •  |    •      •          •       •     •  || |  • ||
   •
   4966              4983                                    5024   5032
                                                             5024   5032
                                                             5025   5033
                                                              5027
                                                                    5032

SfaN I                         Alu I                Acc I
       |                              |                    |
aatttgatgcttcaacaacaacaacaacaacaacaacaaagctcccaacagtaattgaaaggtctacttttgatttt
5120 ttaaactacgaagttgttgttgttgttgttgttgttgtttcgagggttgtcattaactttccagatgaaaactaaaa
     |      •         •        •       •   |    •       •     |    •
   •
    5046                                    5083                  5105
     Mse I
 Mse I
   |    |
 tttaattttaattggcaaatatatgcccatttgtattatctttagtctaatagcgttttcttttttttccagt
 5194
 aaattaaaattaaccgtttatatacgggtaaaacataatagaaaatcagattatcgcaaaagaaaaaaaggtca
  |     | •     •        •        •        •        •         •        •
 5122
      5128
```

FIG. 1-23

Primer 1 INT1 5' Primer

5'-CGCTATA*GAGCTC*AATTTTTAATAAAGAATCAGTAGATCT-3'

Primer 2 INT1 3' Primer

5'-AGCGTATA*GGGCCC*GAGATAATACAAAATGGGCATATATTTGCCA-3'

Primer 3 Vk - 5'

5'-CCCG*TCTAGA*GGAGAYATYGTWATGACCCAGTCTCCA-3'

Primer 4 Vk - 3'

5'-CCC*GTCGAC*CCTTTWAATTCCAGCTTWGTSCC-3'

Primer 5 VH - 5'

5'-CGG*GTCGAC*TTCCGGTAGCGGCAAATCCTCTGAAGGCAAAGGTSAGGTSCAGCTGSAGSAGTCTGG3'

Primer 6 VH - 3'

5'-TGMRGAGAC*GGATCC*GTRGTYCCTTGGCCCCAG-3'

Primer 7 I - Domain Removal Primer

5'-TTGTTCTTGTTCCTGTGTTTGCCTTTGC*GGCCGATCGCAGGATCC*TGGAACTGAAGCATTTGTATCTTCATC-3'

R = A or G
Y = C or T
W = A or T
S = C or G
K = G or T
M = A or C

FIG. 2

Human interin structure (adapted from Humphries 2000).

SEQUENCE LISTING

```
<160> NUMBER OF SEQ ID NOS: 8

<210> SEQ ID NO 1
<211> LENGTH: 5194
<212> TYPE: DNA
<213> ORGANISM: Candida albicans

<400> SEQUENCE: 1 cccaaaaag  ataaaataaa  aacaaaacaa  aacaaaagta  ctaacaaatt  attgaaactt      60 ttaatttta  ataaagaatc  agtagatcta  ttgttaaaag  aaatgaactc  aactccaagt     120
aaattattac  cgatagataa  acattctcat  ttacaattac  agcctcaatc  gtcctcggca    180
tcaatattta  attccccaac  aaaaccattg  aatttcccca  gaacaaattc  caagccgagt    240
ttagatccaa  attcaagctc  tgatacctac  actagcgaac  aagatcaaga  gaaagggaaa    300
gaagagaaaa  aggacacagc  ctttcaaaca  tcttttgata  gaaattttga  tcttgataat    360
tcaatcgata  tacaacaaac  aattcaacat  cagcaacaac  agccacaaca  acaacaacaa    420
ctctcacaaa  ccgacaataa  tttaattgat  gaattttctt  ttcaaacacc  gatgacttcg    480
```

-continued

```
actttagacc taaccaagca aaatccaact gtggacaaag tgaatgaaaa tcatgcacca       540
acttatataa atacctcccc caacaaatca ataatgaaaa aggcaactcc taaagcgtca       600
cctaaaaaag ttgcatttac tgtaactaat cccgaaattc atcattatcc agataataga      660
gtcgaggaag aagatcaaag tcaacaaaaa gaagattcag ttgagccacc cttaatacaa      720
catcaatgga aagatccttc tcaattcaat tattctgatg aagatacaaa tgcttcagtt      780
ccaccaacac caccacttca tacgacgaaa cctactttg cgcaattatt gaacaaaaac       840
aacgaagtca atctggaacc agaggcattg acagatatga aattaaagcg cgaaaatttc      900
agcaatttat cattagatga aaaagtcaat ttatatctta gtcccactaa taataacaat      960
agtaagaatg tgtcagatat ggatctgcat ttacaaaact tgcaagacgc ttcgaaaaac     1020
aaaactaatg aaaatattca caatttgtca tttgctttaa aagcaccaaa gaatgatatt     1080
gaaaacccat taaactcatt gactaacgca gatattctgt taagatcatc tggatcatca     1140
caatcgtcat tacaatcttt gaggaatgac aatcgtgtct tggaatcagt gcctgggtca     1200
cctaagaagg ttaatcctgg attgtctttg aatgacggca taagggggtt ctctgatgag     1260
gttgttgaat cattacttcc tcgtgactta tctcgagaca aattagagac tacaaaagaa     1320
catgatgcac cagaacacaa caatgagaat tttattgatg ctaaatcgac taataccaat     1380
aagggacaac tcttagtatc atctgatgat catttggact cttttgatag atcctataac     1440
cacactgaac aatcaatttt gaatcttttg aatagtgcat cacaatctca aatttcgtta     1500
aatgcattgg aaaaacaaag gcaaacacag gaacaagaac aaacacaagc ggcagagcct     1560
gaagaagaaa cttcgtttag tgataatatc aaagttaaac aagagccaaa gagcaatttg     1620
gagtttgtca aggttaccat caagaaagaa ccagttctgg ccacggaaat aaaagctcca     1680
aaaagagaat tttcaagtcg aatattaaga ataaaaaatg aagatgaaat tgccgaacca     1740
gctgatattc atcctaaaaa agaaaatgaa gcaaacagtc atgtcgaaga tactgatgca     1800
ttgttgaaga aagcacttaa tgatgatgag gaatctgaca cgacccaaaa ctcaacgaaa     1860
atgtcaattc gttttcatat tgatagtgat tggaaattgg aagacagtaa tgatggcgat     1920
agagaagata atgatgatat ttctcgtttt gagaaatcag atattttgaa cgacgtatca     1980
cagacttctg atattattgg tgacaaatat ggaaactcat caagtgaaat aaccaccaaa     2040
acattagcac ccccaagatc ggacaacaat gacaaggaga attctaaatc tttggaagat     2100
ccagctaata atgaatcatt gcaacaacaa ttggaggtac cgcatacaaa agaagatgat     2160
agcattttag ccaactcgtc caatattgct ccacctgaag aattgacttt gcccgtagtg     2220
gaagcaaatg attattcatc ttttaatgac gtgaccaaaa cttttgatgc atactcaagc     2280
tttgaagagt cattatctag agagcacgaa actgattcaa aaccaattaa tttcatatca     2340
atttggcata acaagaaaa gcagaagaaa catcaaattc ataaagttcc aactaaacag     2400
atcattgcta gttatcaaca atacaaaaac gaacaagaat ctcgtgttac tagtgataaa     2460
gtgaaaatcc caaatgccat acaattcaag aaattcaaag aggtaaatgt catgtcaaga     2520
agagttgtta gtccagacat ggatgatttg aatgtatctc aattttacc agaattatct      2580 gaagactctg gatttaaaga tttgaatttt gccaactact ccaataacac caacagacca     2640 agaagttta ctccattgag cactaaaaat gtcttgtcga atattgataa cgatcctaat      2700
gttgttgaac ctcctgaacc gaaatcatat gctgaaatta gaaatgctag acggttatca     2760
gctaataagg cagcgccaaa tcaggcacca ccattgccac cacaacgaca accatcttca     2820
actcgttcca attcaaataa acgagtgtcc agatttagag tgcccacatt tgaaattaga     2880
```

-continued

```
agaacttctt cagcattagc accttgtgac atgtataatg atattttga tgatttcggt    2940 gcgggttcta aaccaactat aaaggcagaa ggaatgaaaa cattgccaag tatggataaa    3000
gatgatgtca agaggatttt gaatgcaaag aaggtgtga ctcaagatga atatataaat    3060
gccaaacttg ttgatcaaaa acctaaaaag aattcaattg tcaccgatcc cgaagaccga    3120
tatgaagaat tacaacaaac tgcctctata cacaatgcca ccattgattc aagtatttat    3180
ggccgaccag actccatttc taccgacatg ttgccttatc ttagtgatga attgaaaaaa    3240
ccacctacgg ctttattatc tgctgatcgt ttgtttatgg aacaagaagt acatccgtta    3300
agatcaaact ctgttttggt tcacccaggg gcaggagcag caactaattc ttcaatgtta    3360
ccagagccag attttgaatt aatcaattca cctgctagaa atgtgctgaa caacagtgat    3420
aatgtcgcca tcagtggtaa tgctagtact attagtttta accaattgga tatgaatttt    3480
gatgaccaag ctacaattgg tcaaaaaatc aagagcaac ctgcttcaaa atccgccaat    3540
actgttcgtg gtgatgatga tggattggcc agtgcacctg aaacaccaag aactcctacc    3600
aaaaaggagt ccatatcaag caagcctgcc aagctttctt ctgcctcccc tagaaaatca    3660
ccaattaaga ttggttcacc agttcgagtt attaagaaaa atggatcaat tgctggcatt    3720
gaaccaatcc caaaagccac tcacaaaccg aagaaatcat ccaaggaaa cgagatttca    3780 aaccataaag tacgagatgg tggaatttca ccaagctccg gatcagagca tcaacagcat    3840
aatcctagta tggtttctgt tccttcacag tatactgatg ctacttcaac ggttccagat    3900
gaaaacaaag atgttcaaca caagcctcgt gaaaagcaaa agcaaaagca tcaccatcgc    3960
catcatcatc atcatcataa acaaaaaact gatattccgg gtgttgttga tgatgaaatt    4020
cctgatgtag gattacaaga acgagcaaa ttattcttta gagttttagg aattaagaat    4080
atcaatttac ccgatattaa tactcacaaa ggaagattca ctttaacgtt ggataatgga    4140
gtgcattgtg ttactacacc agaatacaac atggacgacc ataatgttgc cataggtaaa    4200
gaatttgagt tgacagttgc tgattcatta gagtttattt taactttgaa ggcatcatat    4260
gaaaaccctc gtggtacatt agtagaagtg actgaaaaga agttgtcaa atcaagaaat    4320 agattgagtc gattatttgg atcgaaagat attatcacca cgacaaagtt tgtgcccact    4380
gaagtcaaaa tacctgggc taataagttt gctcctgatg gttcatttgc tagatgttac    4440
attgatttac aacaatttga agaccaaatc accggtaaag catcacagtt tgatctcaat    4500
tgttttaatg aatgggaaac tatgagtaat ggcaatcaac caatgaaaag aggcaaacct    4560
tataagattg ctcaattgga agttaaaatg ttgtatgttc cacgatcaga tccaagagaa    4620
atattaccaa ccagcattag atccgcatat gaaagcatca atgaattaaa caatgaacag    4680
aataattact ttgaaggtta tttacatcaa gaaggaggtg attgtccaat ttttaagaaa    4740
cgttttttca aattaatggg cacttcttta ttggctcata gtgaaatatc tcataaaact    4800
agagccaaaa ttaatttatc aaaagttgtt gatttgattt atgttgataa agaaaacatt    4860
gatcgttcca atcatcgaaa tttcagtgat gtgttattgt tggatcatgc attcaaaatc    4920
aaatttgcta atggtgagtt gattgatttt tgtgctccta taaacatga aatgaaaata    4980 tggattcaaa atttacaaga aattatctat agaaatcggt tcagacgtca accatgggta    5040
aatttgatgc ttcaacaaca acaacaacaa caacaacaac aaagctccca acagtaattg    5100
aaaggtctac ttttgatttt tttaatttta attggcaaat atatgcccat tttgtattat    5160
cttttagtct aatagcgttt tcttttttc cagt                                 5194
```

<210> SEQ ID NO 2
<211> LENGTH: 40
<212> TYPE: DNA
<213> ORGANISM: Artificial sequence
<220> FEATURE:
<223> OTHER INFORMATION: PCR primer

<400> SEQUENCE: 2
cgctatagag ctcaattttt aataaagaat cagtagatct         40

<210> SEQ ID NO 3
<211> LENGTH: 45
<212> TYPE: DNA
<213> ORGANISM: Artificial sequence
<220> FEATURE:
<223> OTHER INFORMATION: PCR primer

<400> SEQUENCE: 3
agcgtatagg gcccgagata atacaaaatg gcatatatt tgcca     45

<210> SEQ ID NO 4
<211> LENGTH: 37
<212> TYPE: DNA
<213> ORGANISM: Artificial sequence
<220> FEATURE:
<223> OTHER INFORMATION: PCR primer

<400> SEQUENCE: 4
cccgtctaga ggagayatyg twatgaccca gtctcca             37

<210> SEQ ID NO 5
<211> LENGTH: 32
<212> TYPE: DNA
<213> ORGANISM: Artificial sequence
<220> FEATURE:
<223> OTHER INFORMATION: PCR primer

<400> SEQUENCE: 5
cccgtcgacc ctttwaattc cagcttwgts cc                  32

<210> SEQ ID NO 6
<211> LENGTH: 66
<212> TYPE: DNA
<213> ORGANISM: Artificial sequence
<220> FEATURE:
<223> OTHER INFORMATION: PCR primer

<400> SEQUENCE: 6
cgggtcgact tccggtagcg gcaaatcctc tgaaggcaaa ggtsaggtsc agctgsagsa     60
gtctgg                                                               66

<210> SEQ ID NO 7
<211> LENGTH: 33
<212> TYPE: DNA
<213> ORGANISM: Artificial sequence
<220> FEATURE:
<223> OTHER INFORMATION: PCR primer

<400> SEQUENCE: 7
tgmrgagacg gatccgtrgt yccttggccc cag                 33

<210> SEQ ID NO 8
<211> LENGTH: 72
<212> TYPE: DNA
<213> ORGANISM: Artificial sequence -continued

```
<220> FEATURE:
<223> OTHER INFORMATION: PCR primer

<400> SEQUENCE: 8
ttgttcttgt tcctgtgttt gcctttgcgg ccgatcgcag gatcctggaa ctgaagcatt      60
tgtatcttca tc                                                         72
```

CHIMERIC CELL-TARGETING PATHOGENIC ORGANISM AND METHOD OF THERAPEUTIC USE

CROSS REFERENCE TO RELATED APPLICATIONS

This application is a divisional application of U.S. application Ser. No. 10/002,389 filed Nov. 30, 2001, now U.S. Pat. No. 6,638,756; which claims priority under 35 USC §119(e) to U.S. Application Ser. Nos. 60/297,995 filed Jun. 13, 2001, now abandoned and 60/251,253 filed Dec. 5, 2000, now abandoned. The disclosure of each of the prior applications is considered part of and is incorporated by reference in the disclosure of the application.

FIELD OF THE INVENTION

This invention relates to treatment of diseases characterized by production of cell surface markers using antibody-targeted compositions. More particularly, this invention relates to chimeric organisms that express an antibody fragment and to the use of such chimeric organisms in treatment of diseases characterized by production of cell surface markers.

BACKGROUND OF THE INVENTION

Many recent gene therapy approaches have exploited the specificity of antibody binding to target cancer cell lines in order to deliver either drugs or immune responses to an actual tumor location. Most cancer cell lines misregulate cell surface proteins and polysaccharides, and are thus easily distinguished from normal somal cells by antibodies (R. E. Hawkins et al., *Gene Therapy* (1998), 5:1581–1583). It is apparent that established carcinomas have successfully avoided activating the immune response within their hosts. Direct attempts to rectify this by recruiting the body's humoral immune response to tumors by injection of murine derived antibodies can unfortunately cause serious and even life threatening human anti-mouse responses (R. K. Jain et al., *J Natl. Cancer Inst.* (1989) 81:570–576 and D. Colcher et al., *J. Natl. Cancer Inst.* (1990) 82:1191–1197). In addition, the overall penetration of antibodies into tumors is limited due to the high molecular weights of these molecules (K. A. Chester et al., *Adv. Drug Delivery Rev.* (1996) 22:303–313).

In an attempt to limit both the size of the antibody and the mouse-character of the antibody, single chain antibodies (scFvs) that encapsulate the binding features of the Fv region of the antibody without the bulk of the native antibody sequence in the c1, c2, and c3 domains have been developed. One methodology to generate scFvs involves tethering the antigen binding domains of $V_H$ and $V_L$ together using a short flexible peptide linker (R. E. Bird et al., *Science* (1988) 242:423–426). Another approach involves the generation de novo of molecular diversity, instead of generating monoclonal antibodies in mice. By using combinatorial antibody libraries on the surface of filamentous bacteriophage screened against immobilized antigen, a single polypeptide chain that is amenable to fusion with other proteins can be generated (J. S. Huston et al., *Proc. Natl. Acad. Sci. USA* (1988) 85:5879–5883; J. McCafferty, *Nature* (1990) 348:552–554; R. H. J. Begent et al., *Nature Med.* (1996) 2:979–984, reviewed in K. A. Chester et al., *Adv. Drug Delivery Rev.* (1996) 22, 303–313). The scFvs obtained by either methodology above show better tumor penetration, but therapeutic application is still in early stages (G. Reitmuller et al., *Lancet* (1994) 343:1177–1183). However, fusions between imaging agents and scFvs have found wide acceptance and extensive application in tumor imaging and radiochemotherapeutic delivery (see J. Bhatia et al., *Cancer* (1999) 85:571–577 and A. M. Wu et al., *Tumor Targeting* (1999) 4:47–58 and references therein).

Antibody recognition has also been used to target cancer cells by incorporation of an scFv into the envelope protein of a retrovirus (S. J. Russell et al., *Nuc. Acids Res.* (1993) 21:1081–1085 and F. Martin et al., *Human Gene Therapy* (1998) 9:737–746). This targeting is modest, but offers some promise, as has been demonstrated for certain types of melanoma (Martin 1998). In addition, adenovirus infection has been used to allow the transient expression of tumor-targeting scFv fusion proteins in whole organisms with moderate success (H. A. Whittington et al., *Gene Therapy* (1998) 5:770–777). Unfortunately, low survivability of adenoviruses carrying antibody generating expression vectors limits their impact.

The most promising therapeutic techniques relying on the specificity of antibody binding focus on engineering T-cells that express antibody fragments fused to surface proteins, and are thus directed to tumor surfaces (recent work reviewed in F. Paillard, *Human Gene Therapy* (1999) 10:151–153). Some of these T-cells are at present in clinical trials. Strategies used to date, however, have drawbacks, including limited efficacy against established tumors, though demonstrating some slowing of tumor metastasis (R. P. McGuinness et al, *Human Gene Therapy* (1999) 10:165–173). Limited effectiveness against established tumors may be due to the inability of the T-cells to penetrate solid cell masses (Paillard 1999). True protection against establishment of invasive carcinoma was obtained only by coinjection of modified T-cells with the tumorogenic line. In clinical applications, this may permit stabilization and localization of established tumors, but not reductive treatment. Another potential problem is that suicide signals T-cells use to induce apoptosis, like tumor necrosis factor I, are often not functional against carcinomas. Even when they are effective, successful cancer cell lines will rapidly adapt to apoptotic signals, and have even been known to induce apoptosis in attacking T-cells (K. Shiraki, *Proc. Natl. Acad. Sci. USA* (1996) 94:6420–6425). In addition, T-cells bearing these chimeras are assembled separately for each patient ex vivo due to possible MHC incompatibilities that could result in serious allergic reactions were T-cells from other humans introduced therapeutically.

*Candida albicans* is the most commonly isolated invasive fungal pathogen in humans. This organism is representative of several that switch between two major classes of morphology. The first morphology is the ellipsoid blastospore. Like most yeast, *C. albicans* assumes this architecture when growing non-pathogenically. Upon binding of *C. albicans* to mammalian tissues (i.e. via the I domain of the INT-1 protein), the cell morphology switches to various filamentous forms, including germ tubes and hyphae, that are capable of aggressively invading host tissue (reviewed by R. A. Calderone, *Microbol. Rev.* (1991) 55, 1–20). Systemic infection of a vulnerable host by *C. albicans* results in high levels of mortality. For example, more than 30% of immunocompromised HIV patients are systemically infected despite appropriate treatment regimes. In addition, *C. albicans* infection commonly leads to death in premature infants, diabetics, and surgical patients. To date, the ability of this pathogenic organism to infect cells when the cell morphology switches to a filamentous form has not been utilized for therapeutic purposes, such as in cancer therapy.

Thus, the need exists in the art for new and better compositions and methods of their use for treating various types of cancers and other diseases associated with production of an abnormal protein.

SUMMARY OF THE INVENTION

The present invention overcomes these and other problems in the art by providing chimeric organisms having a chimeric surface integrin-like protein in which the I domain has been replaced by an antibody fragment that binds a disease-associated antigen on a cell. Binding of the antibody fragment to the disease-associated antigen on the cell triggers virulent transformation of the chimeric pathogenic organism and allows the organism to infect the cell.

In one embodiment according to the present invention, there are provided chimeric pathogenic C. albicans modified to contain an integrin1 (INT1) fusion protein in which the I domain is replaced by an antibody fragment that binds to a disease-associated antigen on a diseased cell. The chimeric C.albicans further contains a disabled wild-type high affininity iron transporter (CAFTR) gene, and a DNA construct comprising a wild-type CAFTR gene under the control of an enhanced filamentous growth protein (EFG1p) response element, wherein binding of the antibody to the disease-associated antigen triggers expression of the CAFTR gene in the DNA construct and filamentous transformation in the chimeric pathogenic C. albicans.

In another embodiment according to the present invention, there are provided methods for treating a disease associated with the presence of cells having a disease-associated surface antigen in a subject in need thereof by administering to the subject a therapeutically effective amount of an invention chimeric pathogenic organism so as to cause binding of the antibody fragment to the disease-associated antigen on the cells, thereby treating the disease by triggering infiltration of the chimeric pathogenic C. Albicans into the cells without substantial damage to healthy cells.

In yet another embodiment, the present invention provides methods for generating a chimeric therapeutic organism from a pathogenic organism that possesses in the wild-type an integrin-like protein with an I domain. In the invention methods, the I domain in the integrin-like protein of the pathogenic organism is replaced with an antibody fragment that binds to a disease-associated antigen on a diseased cell. In the chimeric therapeutic organism, virulent transformation occurs upon binding of the antibody fragment to the disease-associated antigen on the cell.

A BRIEF DESCRIPTION OF THE DRAWINGS

FIGS. 1—1 to 1–23 show the nucleotide sequence of the gene that encodes the integrin-like INT1 protein C. Albicans (GenBank Accession #U35070) (SEQ ID NO:1).

FIG. 2 shows the nucleotide sequences of seven primers used in construction of the chimeric C. albicans of Example 1 (SEQ ID NOS:2 through 8, respectively).

FIG. 3 is a schematic drawing showing human integrin structure (adapted from M. J. Humphries, Biochem. Soc. Trans. (2000) 28:311–340).

Figure 4:
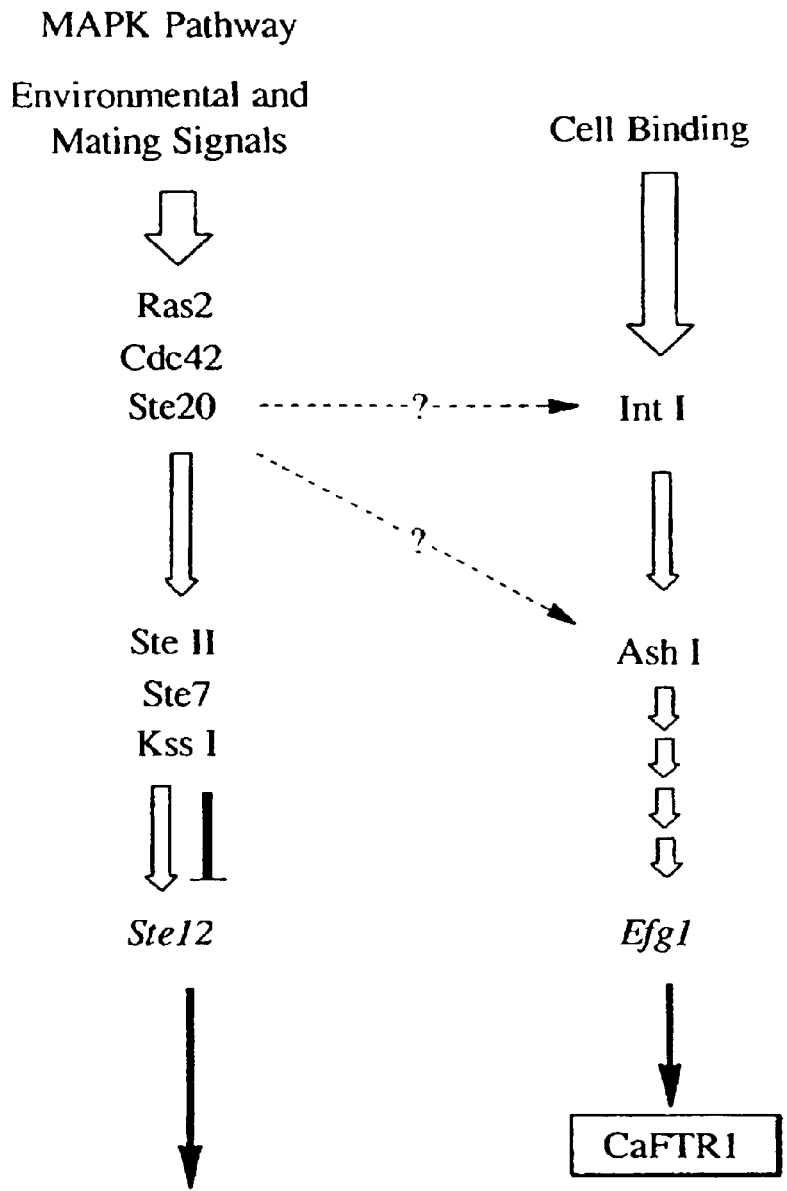

FIG. 4 is a schematic drawing showing two pathways by which hyphal development in yeast is regulated.

DETAILED DESCRIPTION OF THE INVENTION

The present invention provides chimeric pathogenic organisms derived from wild type organisms wherein virulent transformation of the organism is controlled in the wild-type organism by binding of the I domain of a surface integrin-like protein to a cell. The invention chimeric organism comprises a chimeric surface integrin-like protein in which the I domain is replaced by an antibody fragment that binds a disease-associated antigen on a cell. Binding of the antibody fragment to the disease-associated antigen triggers virulent transformation of the chimeric pathogenic organism so as to cause the organism to infiltrate the cell. Virulent invasion of the cell by the chimeric pathogen inhibits growth of the diseased cell.

The invention pathogenic chimeric organism represents a new approach to employing otherwise pathogenic organisms to assist in disease treatment. Although the present invention is described for illustrative purposes with reference to a reingeneered C albicans, suitable pathogenic organisms in addition to C. albicans that can be engineered according to the methods disclosed herein are pathogenic organisms that become virulent (e.g., switch to a filamentous invasive form) upon binding of its integrin-like surface protein (i.e., a cell-cell communication protein) to a target on another cell and in which the binding domain of the surface protein can be replaced with a antibody fragment that binds to a desired target cell associated with a disease state. Preferably the chimeric pathogen also is relatively harmless to mammalian cells until binding of the antibody fragment contained in its surface protein.

In higher eukaryotes, integrins are one of the most important classes of surface proteins responsible for intercellular communication (reviewed in F. G. Giancotti Science (1999) 285:1028–1032 and M. J. Humphries, Biochem. Soc. Trans. (2000) 28:311–340). Generally, integrins are heterodimers, each subunit of which consists of a cytosolic domain with one tyrosine used as a kinase regulatory site, a transmembrane domain, and four EFG-like repeats. As used herein, the term "integrin-like protein" refers to a cell-cell communication transmembrane protein that contains one or more of the above features.

There are various other domains on the integrin proteins, including metal binding MIDAS loops and β propeller domains. Notably, in nine of the fifteen human integrin I subunits, there is a protruding region known alternately as the IA, or the I domain, which appears to regulate integrin targeting. This suggests that the absence or presence of the I domain has little, if any, effect on the integrin's ability to transduce signals, but instead regulates which signals are transduced. The I domain is the only region whose structure has been solved crystallographically (both bound to its target proteins and unbound). Based on these studies, it is believed that the I domain alone is indeed sufficient for binding to collagen (J. Emsley Cell (2000) 101:47–56).

In the invention chimeric organism, the endogenous binding region of the surface integrin-like protein, which non-specifically targets cells (e.g., those containing fibrinogen), is replaced with an antibody fragment, such as a single chain antibody. As a result, rather than nonspecifically binding to any cell containing a binding site for the endogenous binding region, the invention chimeric pathogen binds with specificity to cells that express the target antigen. Binding of the chimeric pathogen to a cell containing an epitope for the antibody fragment triggers virulent invasion of the disease-associated cell. Other cells (e.g., healthy cells) are not bound by the chimeric organism. As a result, pathogenic infiltration of non-targeted cells does not take place.

In one embodiment, the invention provides a chimeric pathogenic C. albicans comprising an INT1 fusion protein in which the I domain is replaced by an antibody fragment that binds to a disease-associated antigen on a cell. Preferably, the INT1 protein in the invention pathogenic organism is a fusion protein in which a single chain antibody replaces the native I domain. The nucleotide sequence encoding INT1 is shown in FIGS. 1A–W (SEQ ID NO:1 herein). Construction of such a chimeric INT1 is described in Example 1 below.

As used herein, the term "disease-associated antigen" means either that the antigen is not expressed in normal, healthy cells, or that the antigen is expressed in abnormal quantity in diseased cells. Existence of disease-associated antigen on cells greatly increases the amount of the chimeric pathogen that attacks such disease-associated cells.

Preferably the antibody fragment is a single chain antibody (scFv), ), but Fv and CDR fragments can also be used. The antibody fragment is preferably incorporated into the surface integrin-like protein to form a fusion protein.

In a preferred embodiment, the chimeric pathogen is a chimeric *Candida albicans,* the most common fungal pathogen of humans. In immunocompromised individuals, *C. albicans* is a dangerous, and sometimes lethal pathogen. The primary protein responsible for *C. albicans* targeting is an integrin-like transmembrane protein known as INT1. INT1 contains an integrin-like domain (known as the I domain), which is the putative targeting region of this protein. FIGS. 1A–W show the nucleotide sequence of the gene that encodes the integrin-like INT1 protein of *C. Albicans* (GenBank Accession # U35070) (SEQ ID NO:1).

The preferred antibody fragment for incorporation into the INT1 protein as a fusion protein is a single chain antibody (scFv), but Fv and CDR fragments can also be used. Thus, in this embodiment, the power and specificity of scFv antibody fragments, which now exist against a considerable number of cell surface targets in cancer cell lines, is combined with the ability to not only bind to the cancer cell mass, but to invade and destroy tumors aggressively and selectively in a manner independent and complementary to the body's own defenses.

The present invention exploits the mechanism involved in the filamentous transformation of *C. albicans* and similar pathogenic organisms, which is controlled by a regulatory system similar to that used by *Saccharomyces cerevisiae* to alter its own morphology under nitrogen starvation conditions and agar invasive conditions. The evolutionary conservation of this pathway has greatly facilitated deconvoluting the biochemistry involved, and recent research has resulted in a better understanding of proteins responsible for *C. albicans* intercellular binding and pathogenicity. In particular, INT1 is the previously known but unidentified surface protein that is strongly crossreactive with antibodies for certain leukocyte integrins, and appears to be the primary protein responsible for attaching to target cells (C. A. Gale et al., *Science* (1998) 279:1355–1358). INT1 is a transmembrane surface protein isolated by cDNA screening of the *C. albicans* genome by oligonucleotide probes derived from the conserved region of human integrins (C. Gale et al., *Proc. Natl. Acad. Sci. USA* (1996) 93:357–361). Over the last fifteen years, many reports have appeared in the literature describing surface proteins that are related to I-subunits of the leukocyte integrins IM/l2 (Mac-1; CD11b/CD18) and IX/θ2 (p150,95; CD11c/CD18) (C. M. Bendel, *J. Clin Invest.* (1993) 92:1840–1849 and references therein). Many monoclonal antibodies that recognize epitopes of these leukocyte surface proteins cross react to blastospores and germ tubes of *C. albicans,* sometimes with the same affinity as to the original human targets.

Upon ligand binding, INT1 signals cell morphology changes that induce hyphae growth. This signaling pathway appears to be largely independent of the mating factor MAPK pathway, which is most commonly associated with morphologic changes. Unlike the pathway that is triggered by ligand binding, the MAPK pathway is triggered by environmental stimulation, such as changes in pH, temperature, mating signaling or nutrient availability, and terminates in transcription factor STE12 in *S. cerevisiae* (Gale 1996; C. J. Gimeno et al., *Cell* (1992) 68, 1077–1090 1992 and R. L. Roberts et al., *Genes Dev.* (1994) 8, 2974–2985) (FIG. 4).

The second pathway to hyphal morphology, which is less well characterized, depends on direct stimulation by serum. Addition of mammalian serum to an otherwise spheroplast culture of *C. albicans* induces hyphae growth, even when the signaling cascade terminating in STE12 (briefly described above) is completely knocked out (Lo 1997). INT1 instead communicates morphology changes via a second, STE12 independent, pathway that appears to have as an intermediary protein Ash1. Ash 1 is a daughter cell-specific protein that helps regulate filamentous growth, and may interact with STE20 (S. Chandarlapaty et al., *Mol. Cell Biol.* (1998) 18, 2884–2891). This pathway terminates at the transcriptional level in a bHLH class protein known as PHD1 recently isolated in *S. cerevisiae.* The homologous protein in *C. albicans* is known as EFG1. The sequence for EFG1 is fully described in W. R. Stoldt et al., *EMBO Journal* (1997) 16, 1982–1991, which is incorporated herein by reference in its entirety.

For both *S. cerevisiae* and *C albicans,* overexpression of their respective analog is sufficient to induce hyphae growth (Stoldt 1997). Importantly, elimination of filamentous growth can only be achieved after disabling both of these two pathways. This observation also rules out a third pathway for signaling.

In construction of the illustrative *C. albicans* chimeric pathogen, the integrin homolog INT1 was isolated using conserved transmembrane sequences from mammalian integrins to clone the cDNA copy of the gene in *C. albicans.* Removal of the INT1 protein reduces specific adhesion of *C. albicans* to HeLa cells by 39%. Therefore, though INT1 is a critical protein for binding to a target, other proteins as well must serve to help mediate this interaction (vide infra), though these proteins have yet to be identified. Still, previous research appears to be consistent with cell surface binding by a single, integrin-like protein of approximate MW of 165 kDa. Interestingly, transgenic experiments where INT1 was overexpressed on the surface of *Saccharomyces cerevisiae,* a nonadhesive and nonpathogenic species, caused strong adhesion to mammalian cells. Thus, INT1 alone is sufficient for target binding.

Deletion of the INT1 gene cripples filamentous growth of *Candida,* though not entirely eliminating it. It has been shown that invasive growth of this type is necessary for parasitic microorganisms to successfully invade host tissues (W-S Lo et al., *Mol. Biol. Cell* (1998) 9:161–171). In vivo testing of the pathogenicity of an INT1 of pathogenicity of the INT1 deletion strain of *C. albicans* on mice was conducted and showed a dramatic reduction in mouse lethality compared to wild-type strains (Gale 1996).

The similarity of INT1 in *C. albicans* to mammalian integrins is not limited to antibody cross reactivity and sequence similarity in the transmembrane region. Notably, INT1 also appears to contain numerous motifs similar by homology to mammalian integrin motifs. These include (1)

two FE-hand divalent cation binding sites that likely mediate target binding; (2) a single cytosolic tyrosine for kinase signaling; and, most importantly, (3) a region that appears to be homologous to the I domain of integrins. Similar to the higher mammalian IM and IX that recognize iC3b and fibrinogen, the I domain like region in C. albicans INT1 is generally thought to be the binding site that targets iC3b. This is further supported by its ~25% sequence identity with the fibrogen binding domain of Staphylococcus aureus.

In the illustrative preferred embodiment of the invention chimeric pathogen, the I domain of the wild-type INT1 protein, which nonspecifically targets fibrinogen, is replaced with an scFv that targets cancer cells. Many scFvs already have been developed that bind to a wide variety of tumor cells for therapeutic applications. Such studies take advantage of the severe misregulation of surface protein populations in tumors by utilizing scFvs that bind epitopes found in such surface proteins. For example, therapeutic applications involving T-cell, viral, and/or drug targeting has already been proven in vivo using scFvs shown in Table 1 below.

As used herein, the terms "disease- or tumor-associated antigen" and "disease- or tumor-associated epitope" encompass antigens and epitopes, respectively, found in surface proteins produced in large amounts in various types of tumors as well as various types of marker proteins (and the epitopes contained therein) that are found associated with tumor cells and not found associated with normal cells. Representative non-limiting examples of tumors having associated antigens to which antibody fragments (e.g., scFvs) of the invention chimeric pathogens bind includes adenocarcinoma of colon, ovary or breast; cervical cancer, nonmucinous ovarian carcinoma; breast, ovarian, colorectal, and pancreatic cancer, and the like. Invention chimeric pathogenic organisms are incapable of infiltrating a cell in the subject until the antibody fragment in the chimeric integrin-like protein binds to its target epitope, triggering a virulent transformation of the chimeric pathogenic organism. Therefore, the invention chimeric pathogenic organisms are substantially incapable of pathogenic activity, such as infiltration, of cells other than their target cells (e.g., cancer cells).

Preferably, the antibody fragment is a scFv and is introduced in the place of the I domain of INT-1 in C. albicans.

TABLE 1

| ANTIBODY | ANTIGEN | CANCER LINE AND LOCATION | REFERENCES | OTHER |
|---|---|---|---|---|
| CC49 | TAG-72 | Adenocarcinoma (colon, ovarian, breast) | McGuiness 1999 Shu 1993 Kashmiri 1995 | |
| FRP5 | ERBB2 | Breast, ovarian | Moritz 1994 Harwerth 1992 Hynes 1993 | Previously used to construct cytotoxic C-lymphocytes. Also used to direct virus targeting (Galmiche 1997) |
| GA733.2 | EGP-2 | Various | Ren-Heidenreich 2000 | |
| HMN-14 | CEA | Colorectal, breast, pancreas, other | Nolan 1999 | Previously used to construct killer T-cells |
| VFF17 | CD44 | Cervical cancer, lymph metastases | Dall 1997 Hekele 1996 | |
| MOV19 | I-FR | Nonmucinous ovarian carcinoma | Melani 1998 | |
| 7.16.4 | Neu | Breast | Katsumata 1995 Stankovski 1993 Disis 1997 | Antigen (neu) is same as ERBB2, and is protein bound by Herceptin. |
| MLuC1 | L(Y) TAA | Various | Mezzanzanica 1998 | Targets misregulated carbohydrates. Lewis (Y) tumor associated antigen |

By replacing the I domain in the integrin-like surface protein with a scFv that binds to a disease-associated tumor cell, the invention chimeric pathogenic organisms are engineered to take advantage of the severely misregulated production of surface protein populations in tumors. In the present invention, the antibody fragment, preferably as a scFv, is incorporated into the position of the native binding domain of an integrin-like protein (i.e., the creation of a fusion protein that contains the scFv incorporated in the place of the I domain in the wild-type pathogenic organism). Many antibody fragments have already been tested for selective binding to a known tumor-associated antigen, for example, as shown in Table 1. Representative non-limiting examples of tumor associated antigens to which scFvs of the invention chimeric pathogens bind include GAG-72, ERBB2, EGP-2, CEA, CD44, I-FR, neu, the Lewis (Y) tumor associated antigen, and the like.

Once engineered to replace the wild-type binding domain of the INT1 protein with an antigen binding region (e.g. scFv) from cancer-specific antibodies, the invention mutant C. albicans strain will specifically bind to a cancer line dictated by the targeting of the scFv-INT1 fusion protein.

Optionally, in order to direct pathogenicity specifically to the target cell (e.g., a carcinoma cell) a gene in the pathogenic organism from which the chimeric organism is derived that is required for invasive growth is disabled or removed and a DNA construct comprising a reengineered copy of the gene necessary for invasive growth is introduced into the chimeric organism under the regulatory control of a transcription factor that regulates filamentous transformation of the organism. However, the gene removed should be one that does not significantly affect vegetative growth of the organism so that large quantities of this chimeric organism can be produced using standard culture techniques.

For example, in *C albicans,* the wild-type gene is placed under the control of a EFG1p response element. While the CaFTR1 gene is currently preferred for reengineering in *C. albicans,* those of skill in the art can readily substitute for reengineering (i.e., in the place of the CaFTR1 gene) another gene from the pathogenic organism that is essential or preferred for pathogenic invasion.

Preferably, in the invention chimeric *C. albicans,* the wild-type CAFTR gene is either disabled or removed and a DNA construct comprising a wild-type CAFTR gene under the control of a EFG1p response element is introduced. Overexpression of EFG1 in *C. albicans* leads to enhanced filamentous growth in liquid and on solid media. Overexpression of EFG1 by a PCK1p-EFG1 fusion is described by A. Sonneborn, *Infect Immun* (1999) 67:9:4655–60, which is incorporated herein by reference in its entirety (See also, V. R. Stoldt et al., *EMBO J* (1997) 16:8 1982–91). The nucleotide sequence for the CaFTR1 gene of *C. albicans* is found at NCBI GenBank Number AF195775.

CaFTR1 extracts iron from mammalian tissues that withhold metals from microbial predators as a defense mechanism (D. M. DeSilva et al., *Physiol. Rev.* (1996) 76, 31–47 and H. Gunshin et al., *Nature* (1997) 388, 482–488). Removal of the native CaFTR1 completely abrogates pathogenicity. Mice injected with a mutant *C. albicans* having a disabled CaFTR1 gene survive entirely; while those injected with an equal amount of wild-type *C. albicans* do not. Under circumstances of normal unicellular growth in an abundance of iron, though, CaFTR1 is not an essential gene. In conditions where iron is in limited quantities, for instance during circulation through a host designed to have limiting nutrient levels, this gene is highly upregulated. Removal of the CaFTR1 gene only causes a growth (and thus invasion) deficiency when pathogenesis is initiated. This protein is normally regulated entirely independently from the morphology signaling pathway, and its concentration is dependent only on the heavy metals detected in the environment. By placing this protein under the transcriptional control of the cell morphology pathway initiated by INT1, as described herein, the pathogenicity of the overall assembly can be tightly restricted to scFv-INT1 targeted cells.

In this preferred embodiment of the invention chimeric pathogenic organism, binding of the antibody to the disease-associated antigen triggers both expression of the CAFTR gene in the DNA construct and filamentous transformation of the chimeric pathogenic *C. albicans.* Since expression of INT1 in wild-type *C. albicans* is activated by INT1 binding to other cells, placing expression of the *C. albicans* iron transporter under control of the Efg1 expression system ensures that both the pathogenicity and the binding of the invention chimeric organism is directed specifically to target cells. If the antibody fragment incorporated in the place of the INT1 binding domains is specific for a tumor cell, the pathogenicity of the *C. albicans* cell line is directed specifically towards target cancerous cells, and nonspecific toxicity is inhibited. In other words, the virulence of the engineered strain of *C. albicans* will only be activated once scFv-INT1 binds to its target antigen on the surface of the carcinoma.

The gene that triggers filamentous growth can be disabled in the invention chimeric organism using any method known in the art, for example, by disruption of the gene at both diploid loci using standard techniques. The native gene can be reintroduced under the control of a response element (e.g., a transcription factor) that regulates filamentous transformation of the organism using known techniques, such as by use of homologous recombination (as described in Example 1 herein). This regulatory reassignment of the gene that triggers transformation tightly limits the pathogenicity dependent on this protein to the specified target.

In yet another embodiment, the present invention provides methods for treating a disease associated with the presence of cells having a disease-associated surface antigen in a subject in need thereof. The invention method includes administering to the subject, a therapeutically effective amount of an invention chimeric pathogenic organism so as to cause binding of the antibody fragment to the disease-associated antigen on the cell, thereby specifically treating the disease by triggering infiltration of the chimeric pathogenic organism into the cells without substantial damage to healthy cells. The invention method may further include administering to the subject an immunosuppressive agent to inhibit the subject's immune system from destroying the chimeric pathogen prior to achieving a therapeutic effect. Representative immunosuppressive agents useful in the practice of the invention methods include such agents as cyclosporin A, OKT3, FK506, mycophenolate mofetil (MMF), azathioprine, corticosteroids (such as prednisone), antilymphocyte globulin, antithymocyte globulin, and the like. In a preferred embodiment of the invention methods, the invention chimeric pathogen is used to target and attack tumor cells.

In invention therapeutic methods, the chimeric pathogenic organisms are used to infiltrate and destroy both ex vivo cell lines (e.g., tumor cell lines), as well as in vivo murine models of human carcinomas, and the like. The invention pathogenic organisms also have specific utility as research reagents for the testing of therapeutic compositions. For example, the invention chimeric organisms can be used to compare the therapeutic effect against a particular cell line of various antibody fragments engineered into the surface integrin-like protein. Binding of invention organisms to these ex vivo and in vivo models can be tested for efficacy using known assays (e.g., mouse tumor models) to determine binding of the antibody fragment (e.g., single chain antibody) to the target antigen on a disease-associated cell.

The chimeric pathogens used in practice of the invention method can be administered for therapeutic purposes, such as treatment of tumor, by any route known to those of skill in the art, such as intraarticularly, intracisternally, intraocularly, intraventricularly, intrathecally, intravenously, intramuscularly, intraperitoneally, intradermally, intratracheally, intracavitarily, and the like, as well as by any combination of any two or more thereof.

The most suitable route for administration will vary depending upon the disease state to be treated, or the location of the suspected condition or tumor to be treated. For example, for treatment of inflammatory conditions and various tumors, local administration, including administration by injection directly into the body part containing the tumor provides the advantage that the chimeric pathogen can be administered in a high concentration without risk of the complications that may accompany systemic administration thereof.

The chimeric pathogen is administered in "a therapeutically effective amount." An effective amount is the quantity of a chimeric pathogen necessary to aid in treatment, inhibition or destruction of diseased tissue (e.g. tumor) under treatment in a subject. A "subject" as the term is used herein is contemplated to include any mammal, such as a domesticated pet, farm animal, or zoo animal, but preferably is a human. Amounts effective for therapeutic use will, of course, depend on such factors as the size and location of the body part to be treated, the affinity of the antibody fragment for the target antigen, the type of target tissue, as well as the route of administration. Local administration of the targeting construct will typically require a smaller dosage than any mode of systemic administration, although the local concentration of the chimeric pathogen may, in some cases, be higher following local administration than can be achieved with safety upon systemic administration.

The invention composition can also be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1–4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

Preferably the antibody fragment is a scFv incorporated into the chimeric surface protein of the pathogen as a targeting device and is not relied upon as the toxic agent. Rather, it is the pathogenic organism itself that invades and destroys the target cells in accordance with the present invention. A single chain antibody (scFv) is a genetically engineered molecule containing the variable region of the light chain and the variable region of the heavy chain, linked by a suitable polypeptide linker as a genetically fused single chain molecule. Methods of making these fragments are known in the art. (See for example, Harlow & Lane, *Antibodies: A Laboratory Manual,* Cold Spring Harbor Laboratory, New York, 1988, incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

Fv fragments comprise an association of $V_H$ and $V_L$ chains. This association may be noncovalent, as described in Inbar et al., *Proc. Nat'l Acad. Sci. USA* 69:2659, 1972. Alternatively, the variable chains can be linked by an intermolecular disulfide bond or cross-linked by chemicals such as glutaraldehyde. See, e.g., Sandhu, *Crit. Rev. Biotech.* 12:437, 1992; and Singer et al., *J. Immunol.* 150:2844, 1993. Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli.* The recombinant host cells synthesize a single polypeptide chain with a linker peptide bridging the two V domains. Methods for producing scFvs are described, for example, by Whitlow et al., *Methods: a Companion to Methods in Enzymology,* 2: 97, 1991; Bird et al., *Science* 242:423–426, 1988; Pack et al., *Bio/Technology* 11:1271–77, 1993; Sandhu, supra, and Ladner et al., U.S. Pat. No. 4,946,778, which is hereby incorporated by reference in its entirety.

Another form of an antibody fragment suitable for incorporation as a fusion protein in invention chimeric pathogenic organisms is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology,* 2: 106, 1991.

Antibodies that bind to a tumor cell or other disease-associated antigen can be prepared using an intact polypeptide or biologically functional fragment containing small peptides of interest as the immunizing antigen. The polypeptide or a peptide used to immunize an animal (derived, for example, from translated cDNA or chemical synthesis) can be conjugated to a carrier protein, if desired. Commonly used carriers that are chemically coupled to the peptide include keyhole limpet hemocyanin (KLH), thyroglobulin, bovine serum albumin (BSA), and tetanus toxoid, and the like. The coupled peptide is then used to immunize the animal (e.g., a mouse, a rat, or a rabbit).

The preparation of such monoclonal antibodies is conventional. See, for example, Kohler & Milstein, *Nature* 256:495, 1975; Coligan et al., sections 2.5.1–2.6.7; and Harlow et al., in: *Antibodies: a Laboratory Manual,* page 726 (Cold Spring Harbor Pub., 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1–2.7.12 and sections 2.9.1–2.9.3; Barnes et al., Purification of Immunoglobulin G (IgG), in: *Methods in Molecular Biology,* Vol. 10, pages 79–104 (Humana Press, 1992).

Antibodies of the present invention may also be derived from subhuman primate antibodies. General techniques for raising therapeutically useful antibodies in baboons can be found, for example, in Goldenberg et al., International Patent Publication WO 91/11465 (1991) and Losman et al., 1990, *Int. J. Cancer* 46:310, which are hereby incorporated by reference. Alternatively, a therapeutically useful antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833,1989, which is hereby incorporated in its entirety by reference. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993, which are hereby incorporated by reference.

It is also possible to use anti-idiotype technology to produce monoclonal antibodies, which mimic an epitope. For example, an anti-idiotypic monoclonal antibody made to a first monoclonal antibody will have a binding domain in the hyper variable region that is the "image" of the epitope bound by the first monoclonal antibody.

The assembly, selection, and integration of these chimeric scFv-INT1 products are conducted using standard molecular biology, for example as is described in Example 1 herein. The proper assembly of the invention chimeric scFv-INT-1 protein and adhesion to the epitopes in target cell lines, e.g., tumor cell lines, can be tested by introduction of the chimeric assembly into *S. cerevisiae*, preferably under the control of a promoter, such as the actin promoter, that is constantly activated in such yeast cell lines. Yeast cells (e.g., *Saccharomyces cerevisiae*) possess an efficient and precise system for genetic recombination. The natural process of homologous recombination depends on a system of enzymes that search for regions of sequence homology between two DNA molecules (which may be entire chromosomes). Once homology is found, an exchange of information is possible.

Plasmids or other vectors carrying recombinant-DNA (r-DNA) clones which contain naturally-occurring yeast sequences and which are introduced into cells by standard transformation methods are capable of stably integrating into the yeast genome at sites of homology. The efficiency of this process can be increased by up to a thousand-fold by introducing a double-strand break within a DNA sequence on the incoming DNA molecule that is homologous to a sequence resident in the yeast cell. The cloned yeast DNA on the transforming vector is referred to herein as the targeting sequence, and the site of integration is referred to herein as the target site.

In one process described in U.S. Pat. No. 5,783,385 to Treco, et al., which is incorporated herein by reference in its entirety, a targeting DNA molecule, e.g., a bacterial plasmid, which is non-replicating in yeast is introduced into the population of host yeast cells containing the r-DNA. The bacterial plasmid has a selectable marker gene that functions in yeast and a first targeting DNA sequence which is homologous in part to a second target r-DNA clone sequence. Preferentially, the targeting plasmid is cut with a restriction endonuclease that introduces a double-strand break within the targeting sequence, thereby linearizing the bacterial plasmid and providing DNA ends which are recombinogenic to stimulate the process of homologous recombination with host yeast sequences. Because the plasmid is non-replicating in yeast, stable transformation with the selectable marker can only proceed by homologous recombination. The efficiency of transformation by homologous recombination is increased when the plasmid is cut by restriction enzyme digestion within the targeting DNA sequence homologous in part to the target r-DNA sequence.

The host yeast cells are grown under conditions such that only those yeast cells that have been stably transformed, i.e., have had the plasmid and selectable marker stably integrated in the host cell by homologous recombination will be able to grow. In a correctly targeted event, the entire plasmid is stably incorporated contained in the host yeast cell by homologous recombination of the targeting DNA sequence of the plasmid and the homologous target r-DNA clone sequence. Only those few host yeast cells that contain the desired, target r-DNA clone sequence (and have thereby undergone homologous recombination with the targeting plasmid) are able to grow under the new growth conditions, due to the introduction of the yeast-selectable marker gene contained on the targeting plasmid.

The vast majority of the population of the host yeast cells containing r-DNA clone sequences that are not homologous to the targeting DNA sequence contained on the plasmid, do not have the plasmid incorporated by homologous recombination and, therefore, do not acquire the marker gene that is essential for growth under the selection conditions. Therefore, it is preferable that any yeast-selectable marker gene that is contained on the incoming targeting plasmid has been deleted entirely or almost entirely from the genome of the host yeast strain that is used for the vector. This prevents any spurious homologous recombination events between the incoming yeast-selectable marker gene and any other natural yeast genetic loci. If a yeast-selectable marker gene on the incoming targeting plasmid is not deleted from the yeast genome, but is retained as a mutated, non-functional portion of the yeast chromosome, more positive scores for homologous recombination will have to be screened to ensure that the homologous recombination event has taken place between the targeting DNA sequence on the bacterial plasmid and the desired, target r-DNA clone sequence. Cells with the integrated marker can grow into colonies when plated on appropriate selective media.

Alternatively, a yeast-selectable marker gene on the incoming targeting DNA molecule can be a bacterial gene that confers drug resistance to yeast cells, e.g., the CAT or neo genes from Tn9 and Tn903, or bacterial amino acid or amino acid nucleoside prototrophy genes, e.g., the *E. coli* argH, trpC, and pyrF genes.

Methods for plasmid purification, restriction enzyme digestion of plasmid DNA and gel electrophoresis, use of DNA modifying enzymes, ligation, transformation of bacteria, transformation of yeast by the lithium acetate method, preparation and Southern blot analysis of yeast DNA, tetrad analysis of yeast, preparation of liquid and solid media for the growth of *E. coli* and yeast, and all standard molecular biological and microbiological techniques can be carried out essentially as described in Ausubel et al. (Ausubel, F. M. et al., *Current Protocols in Molecular Biology*, Greene Publishing Associates and Wiley-Interscience, New York, 1987).

Once the proper assembly of the invention chimeric scFv-INT-1 protein and adhesion to the epitopes in target cell lines, e.g., tumor cell lines, has been tested in a non-pathogenic yeast cell (e.g., *Saccharomyces cerevisiae*) homologous recombination can be used to insert a polynucleotide sequence encoding the chimeric scFv-INT1 into *Candida albicans*, and similar ex vivo experiments as those performed for *S. cerevisiae* will be performed to assure that replacement of the I domain does not seriously impair the proper folding and targeting of scFv-INT1. At this point, ex vivo experiments verifying adhesion of this mutant *C. albicans* strain to cancer cells are performed, in addition to preliminary in vivo mice experiments to ascertain that this targeting alone is adequate in mice to restrict pathogenicity and targeting to tumors.

The most common model for human cancers is a murine subject that has been transfected with human carcinomas. After an incubation period varying from weeks to months after carcinoma introduction to allow growth of test tumors, transfected mice will be treated with the genetically modified *C. albicans*. Survival of the mice and tumor spreading are monitored over time. Biopsies of the tumorous tissues can also be taken to investigate *C. albicans* invasion. By using large groups of genetically identical mice, aggregate data can be collected.

Evolution has optimized certain organisms to invade mammalian tissue. The present invention harnesses this powerful and highly pathogenic trait to generate a new weapon against cancer and other diseases characterized by the presence of cells with a disease-associated antigen. In contrast to more indirect methodologies previously applied that recruit the natural immune system responses, fusion scFv-INT1 proteins targeted to disease-associated tissues will direct aggressive invasion of the naturally invasive pathogen to diseased host tissue. The method of the present invention is a novel approach to cancer treatment that recruits the previously untapped resource of pathogenic organisms (e.g. fungi) as potent and specific therapy to eliminate diseased tissue characterized by disease-associated antigens.

The invention will now be described by reference to the following non-limiting illustrative example:

EXAMPLE 1

Construction of the scFv-INT1 Fusion Gene

Using bulk genomic DNA from *C. albicans,* primers 1 and 2 (shown in FIGS. 2A–B) (SEQ ID NOS:2 and 3) are used for PCR amplification of the INT1 gene (available from GenBank under accession number U35070) (SEQ ID NO:1) as previously described (Gale 1996). These primers insert SacI and ApaI restriction sites at the 5' and 3' ends of the coding region of INT1, respectively. These restriction sites are both nonexistent in the ORF of the gene (see gene sequence in FIGS. 1A–W). The 5 kB product of this PCR reaction is isolated using a standard Qiagen desalting kit, digested with the appropriate enzymes SacI and ApaI, and ligated into predigested and dephosphorylated pBluescript II SK (+) phagemid plasmid according to the manufacturer's instructions (Product #212205, Stratagene, LaJolla, Calif.). ssDNA incorporating the INT1 gene is then generated using standard techniques with helper phage and uridine in dut⁻ ung⁻ strains of *E. Coli* according to the manufacturer's instructions.

To introduce multiple cloning sites in the ssDNA PCR product in the place of the I domain of INT1, primer 7 (shown in FIGS. 2A–B) (SEQ ID NO:8) is used in a standard polymerase/ligase reaction; also thus eliminating the I domain. Isolation of the generated plasmids is performed using standard techniques.

Single chain antibodies (scFvs) having the target antigen binding region of a desired antigen are generated using reverse transcriptase PCR of the bulk RNA from antibody-generating cell lines using primers 4 to 6 (shown in FIGS. 2A–B) (SEQ ID NOS:5, 6, and 7). The binding regions are subcloned into the cut and dephosphorylated plasmid prepared as described above, and then a fusion gene is isolated and characterized using techniques described in Z. Eshhar et al., *Methods in Enzymology* 8:133–142 (1995), except that Primers 4 to 6 differ from those shown in Eshhar by including different restriction endonuclease sites, as INT1 has restriction sites for the nucleases used by Eshhar. The primers used to remove the binding regions of the heavy and light chains incorporate a linker that allows the now-assembled scFv-INT1 protein to have the binding region activated and folded properly.

The chimeric INT1-scFv fusion protein is directly expressed in *E. Coli* for in vitro studies of folding and binding using known techniques described in Sections 10.0.1 and 16.1 to 16.7 of *Current Protocols in Molecular Biology,* Collected Volumes 1 to 4, edited by Ausubel, F. M. et al., John Wiley &Sons, 2000. In addition, the chimeric INT1-scFv fusion protein is incorporated into *S. Cerevisiae* using an expression plasmid containing the nucleotide sequence that encodes the fusion protein for cell-cell studies and is incorporated back into *Candida albicans* by homologous recombination using techniques described in Section 13.10.3 of *Current Protocols in Molecular Biology,* supra. Thus, a tumor-specific organism is readily accomplished.

It will be apparent to those skilled in the art that various changes may be made in the invention without departing from the spirit and scope thereof, and therefore, the invention encompasses embodiments in addition to those specifically disclosed in the specification, but only as indicated in the appended claims.

What is claimed is:

1. A method for generating a chimeric *Candida* organism from a pathogenic organism that possesses in the wild-type an INT1 protein with an I domain, said method comprising:

replacing the I domain in the INT1 protein of the pathogenic organism with an antibody fragment that binds to a disease-associated antigen on a diseased cell;

wherein the wild-type pathogenic organism undergoes virulent transformation by binding of the I domain of the surface INT1 protein to a cell, and wherein the chimeric *Candida* organism undergoes virulent transformation by binding of the antibody fragment to the disease-associated antigen on the cell.

2. The method of claim 1, wherein the pathogenic organism is *C. albicans* and wherein the method further comprises disabling the wild-type high-affinity iron transporter gene in the *C. albicans,* and introducing a DNA construct comprising a wild-type high-affinity iron transporter gene under the control of a EFG1p response element, wherein binding of the antibody fragment to the disease-associated antigen triggers expression of the high-affinity iron transporter gene in the DNA construct and filamentous transformation in the chimeric pathogenic *C. albicans.*

3. The method of claim 2, wherein the antibody fragment is a single chain antibody.

4. The method of claim 2, wherein the antibody fragment binds to an antigen on a tumor cell.

5. The method of claim 4, wherein the disease-associated antigen is contained in an abnormal surface protein of the tumor cell.

* * * * *